United States Patent [19]
Crystal et al.

[11] Patent Number: 6,013,638
[45] Date of Patent: Jan. 11, 2000

[54] ADENOVIRUS COMPRISING DELETIONS ON THE E1A, E1B AND E3 REGIONS FOR TRANSFER OF GENES TO THE LUNG

[75] Inventors: Ronald G. Crystal, Potomac, Md.; Wilfried Dalemans, Hoegaarden, Belgium; Michel Perricaudet; Leslie Stratford-Perricaudet, both of Ecrosnes, France; Andrea Pavirani, Strasbourg, France

[73] Assignees: The United States of America as represented by the Department of Health and Human Services, Washington, D.C.; Transgene S.A., Strasbourg, France

[21] Appl. No.: 08/165,753

[22] Filed: Dec. 13, 1993

Related U.S. Application Data

[63] Continuation of application No. 07/769,623, Oct. 2, 1991, abandoned.

[51] Int. Cl.⁷ .............................. A61K 48/00; C12N 15/00
[52] U.S. Cl. ......................... 514/44; 514/851; 435/320.1
[58] Field of Search ............................. 514/44; 435/172.3, 435/69.1, 320.1

[56] References Cited

U.S. PATENT DOCUMENTS

| | | | |
|---|---|---|---|
| 4,920,209 | 4/1990 | Davis et al. | 435/235 |
| 4,980,286 | 12/1990 | Morgan et al. | 435/172.3 |

FOREIGN PATENT DOCUMENTS

| | | |
|---|---|---|
| 0 185 573 | 6/1986 | European Pat. Off. . |

OTHER PUBLICATIONS

Karlsson et al., "Stable Gene Transfer and Tissue–Specific Expression of a Human Globin Gene Using Adenoviral Vectors," *EMBO J.*, 5, 2377 (1986).

Haj–Ahmad et al., "Development of a Helper–Independent Human Adenovirus Vector and its Use in the Transfer of the Herpes Simplex Virus Thymidine Kinase Gene," *J. Virol.*, 57, 267 (1986).

Levrero et al., "Hepatitis B Virus (HBV) X Gene Expression In Human Cells and Anti–X Antibodies Detection in Chronic HBV Infection," *Hepadna Viruses*, 237–252 (1987).

Levrero et al., "Defective and Nondefective Adenovirus Vectors for Expressing Foreign Genes in vitro and in vivo," *Science*, 101, 195–202 (1991).

Mansour et al., "Downstream Sequences Affect Transcription Initiation from the Adenovirus Major Late Promoter," *Molecular and Cellular Biology*, 6, 2684–2694 (Jul. 1986).

Riordan et al., "Identification of the Cyctic Fibrosis Gene: Cloning and Characterization of Complementary DNA," *Science*, 245, 1066–1072 (Sep. 1989).

Rommens et al., "Identification of the Cystic Fibrosis Gene: Chromosome Walking and Jumping," *Science*, 245, 1059–1065 (Sep. 1989).

Rosenfeld et al., "In vivo Transfer of the Human Cystic Fibrosis Gene to the Respiratory Epithelium," *Clinical Research*, 39(2), 311A (1991).

Stratford–Perricaudet et al., "Evaluation of the Transfer and Expression in Mice of an Enzyme–Encoding Gene Using a Human Adenovirus Vector," *Human Gene Therapy*, 1, 241–256 (1990).

Ballay et al., "In vitro and in vivo Synthesis of the Hepatitis B Virus Surface Antigen and of the Receptor for Polymerized Human Serum Albumin from Recombinant Human Adenoviruses," *The EMBO J.*, 4, 3861–3865 (1985).

Ballay et al., "Hepatitis B Adenovirus Recombinants as a Potential Live Vaccine," *Hepadna Viruses*, 481–493 (1987).

Chasse et al., "Human Recombinant Adenovirus Used to Correct a Mouse Enzyme Deficiency," Abstract of Paper Presented at Meeting on Regulation of Liver Gene Expression, May 3–May 7 (1989).

Chasse et al., "L'adénovirus: vecteur de thérapie génique?" *M/S Synthese*, 5, 331–337 (1989).

Crystal et al., "New Viral Transfer System," *Pediatric Pulmonology*, 103 (Supplement 5), 103 (1990).

Crystal, R.G., "α1–Antitrypsin Deficiency, Emphysema, and Liver Disease," *The Journal of Clinical Investigation, Inc.*, 85, 1343–1352 (May 1990).

Gilardi et al., "Expression of Human $\alpha_1$–antitrypsin Using a Recombinant Adenovirus Vector," *FEBS Letters*, 267(1), 60–62 (Jul. 1990).

Ginsberg et al., "Role of Early Region 3 (E3) in Pathogenesis of Adenovirus Disease," *Proc. Natl. Acad. Sci. USA*, 86, 3823–3827 (May 1989).

Jaffe et al., "Adenoviral Mediated Transfer and Expression of a Normal Human α1–Antitrypsin cDNA in Primary Rat Hepatocytes," *Clinical Research*, 39(2), 302A (1991).

Jones et al., "Isolation of Adenovirus Type 5 Host Range Deletion Mutants Defective for Transformation of Rat Embryo Cells," *Cell*, 17 683–689 (Jul. 1979).

Kerem et al., "Identification of Mutations in Regions Corresponding to the Two Putative Nucleotide (ATP)–Binding Folds of the Cystic Fibrosis Gene," *Proc. Natl. Acad. Sci. USA*, 87, 8447–8451 (Nov. 1990).

Kerem et al., "Identification of the Cystic Fibrosis Gene: Genetic Analysis," *Science*, 245, 1073–1080 (Sep. 1989).

Venkatesh et al, PNAS USA, vol. 87 (Nov. 1990) pp. 8746–8750.

Rosenfeld et al, Science, vol. 252 (Apr. 19, 1991) pp. 431–434.

Drumm et al, Cell, vol. 62 (Sep. 21, 1990) pp. 1227–1233.
Chasse, J. Cell. Biochem., Supp. 13B (Feb. 1989) p. 174.

(List continued on next page.)

*Primary Examiner*—Deborah Crouch
*Attorney, Agent, or Firm*—Leydig, Voit & Mayer, Ltd.

[57] ABSTRACT

The present invention relates, in general, to a adenovirus mediated transfer of genes to the lung. In particular, the present invention relates to a method of recombinant, replication-deficient adenovirus mediated transfer of desired genes to the lung whereby desired proteins of interest are produced for local and/or systemic use.

14 Claims, 7 Drawing Sheets

OTHER PUBLICATIONS

Long et al (1984) Biochemistry 23, 4828–4837.
Riordan etal (1989) Science 245, 1066–1072.
Crystal et al (1994) Nature Genetics8, 42–51.
Gilardi etal (1990) FEBS Let 267, 60–62.
Rich etal (1990) Nature 347, 358–363.
Ballay etal (1987) Hepadna Viruses, Alan R. Liss, Inc, 481–483.

Blau etal (Nov. 2, 1995) New Eng. J. Med, 1204–1207.

Orkin etal (Dec. 7, 1995) Report and Recommendations . . . on Gene Therapy, 1–41; Office of NIH Publications.

Mulligan (1993) Science 260, 926–932.

Rosenfeld etal (1992) Cell 68, 142–154.

Hay et al (1995) Human Gene Therapy 6, 1487–1496.

ADENOVIRUS COMPRISING DELETIONS ON THE E1A, E1B AND E3 REGIONS FOR TRANSFER OF GENES TO THE LUNG

This is a continuation of application Ser. No. 07/769,623 filed on Oct. 2, 1992 now abandoned.

BACKGROUND OF THE INVENTION

1. Field of the Invention

The present invention relates, in general, to a method of adenovirus mediated transfer of genes to the lung. In particular, the present invention relates to a method of recombinant, replication-deficient adenovirus mediated transfer of desired genes to the lung for the purpose of producing desired proteins of therapeutic or research interest for local or systemic use.

2. Background Information

One of the hurdles to overcome in most forms of somatic gene therapy is the specific delivery of the therapeutic gene (encoding a therapeutic protein) to the organs manifesting the disease. When the lung is the organ to be treated, a functional gene can be delivered directly to the respiratory epithelium by means of tracheal installation. The disadvantage of such an approach is due to the normal biology of the respiratory epithelium; only a small proportion of alveolar and airway epithelial cells go through the proliferative cycle in one day, and a large proportion of the cells are terminally differentiated and are, therefore, incapable of proliferation (Evans, M. J. and Shami, S. G. (1989) In: Lung Cell Biology (C. Lenfant, D. Massaro, Eds.) Marcel Dekker, New York, pp. 1–36). In this regard, it may be difficult to transfer functional genes to the respiratory epithelium by means of vectors (such as retroviruses) that require proliferation of the target cells for expression of the newly transferred gene (Miller, D. G. et al. (1990) Mol. Cell. Biol. 10, 4239).

To circumvent the slow target-cell proliferation, the present invention uses a recombinant adenoviral vector to transfer a recombinant gene to the respiratory epithelium in vivo. Host cell proliferation is not required for expression of adenoviral proteins (Horwitz, M. S. et al. (1990) In: Virology (B. N. Fields and D. M. Knipe, Eds.) Raven Press, New York, ed. 2, pp. 1679–1721 and Berkner, K. L. (1988) Biotechniques 6, 616) and adenoviruses are normally trophic for the respiratory epithelium (Straus, S. E. (1984) In: The Adenoviruses (H. S. Ginsberg Ed.) Plenan Press, New York and London, pp. 451–496).

Other advantages of adenoviruses as potential vectors for human gene therapy are as follows: (i) recombination is rare; (ii) there are no known associations of human malignancies with adenoviral infections despite common human infection with adenoviruses; (iii) the adenovirus genome (which is a linear, double-stranded piece of DNA) can be manipulated to accommodate foreign genes ranging in size from small peptides to up to 7.0 to 7.5 kb in length; and (iv) live adenovirus, having as an essential characteristic the ability to replicate, has been safely used as a human vaccine (Horwitz, M. S. et al. (1990) In: Virology (B. N. Fields and D. M. Knipe, Eds.) Raven Press, New York, ed. 2, pp. 1679–1721; Berkner, K. L. (1988) Biotechniques 6, 616; Straus, S. E. (1984) In: The Adenoviruses (H. S. Ginsberg Ed.) Plenan Press, New York and London, pp. 451–496; Chanock, R. M. et al. (1966) J. Am. Med. Assoc. 195, 151; Haj-Ahmad, Y. and Graham, F. L. (1986) J. Virol. 57, 267; Ballay, A. et al. (1985) EMBO J. 4, 3861).

SUMMARY OF THE INVENTION

It is a general object of this invention to provide a method of producing a protein in the cells of the lung of a patient.

It is another general object of this invention to provide a method for producing a protein in the cells of an animal model system.

It is a specific object of this invention to provide a method of producing a protein in the cells of the lung of a patient. The method comprises administering to the patient's lung a replication deficient adenovirus comprising a DNA segment encoding the protein under conditions such that the protein is produced. Depending on the specific sequences placed into the recombinant adenovirus, the protein may be secreted for local therapy to the lung or retained within the producing cell or secreted for systemic use.

Further objects and advantages of the present invention will be clear from the description that follows.

DETAILED DESCRIPTION OF THE INVENTION

Figure 1:
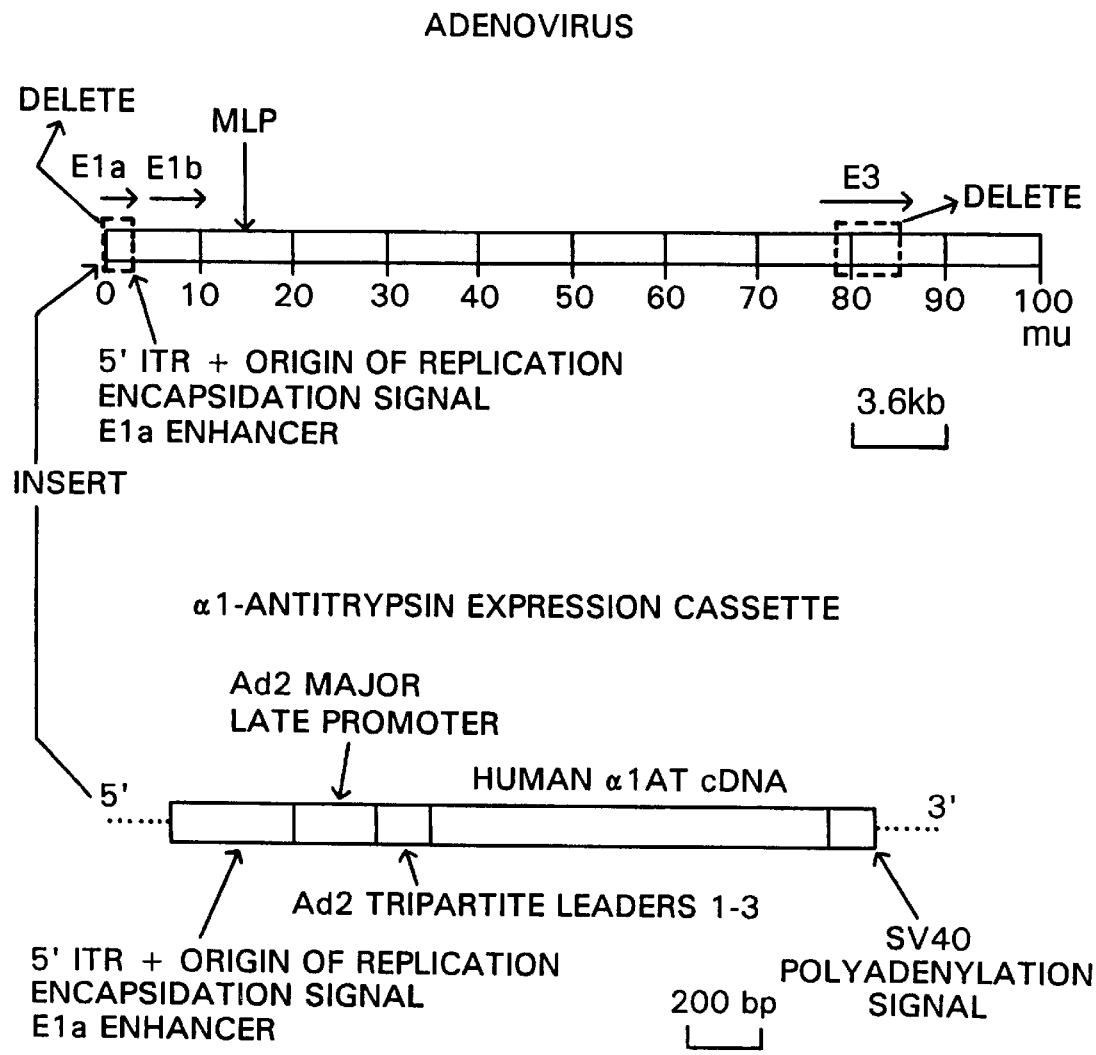
FIG. 1. Recombinant adenovirus (Ad) vector. Top—Wild type Ad type 5 (Ad5) genome showing the Ela, Elb [map units (mu) 1.3 to 11.2; 100 mu=36 kb] and E3 (mu 76.6 to 86.0) regions. Bottom—Details of the α1AT expression cassette. ITR, inverted terminal repeat.

The present invention relates to a method of producing therapeutic proteins in the lung. The terms protein, polypeptide, peptide, or segment of amino acids are herein used interchangeably to define a polymer of amino acids linked through peptide bonds. Therapeutic proteins are defined herein as proteins advantageous to an individual.

As a first step, a replication deficient adenovirus (referred to below as the "modified adenovirus") is constructed with the coding sequences of the protein of therapeutic or research interest. Examples of such proteins include, but are not limited to:

I. Proteins for local use within the lung (in the lumen of the lung on the epithelial surface and/or in the tissues of the lung and/or with the cells of the lung).
   A. Antiproteases
      1. α1-antitrypsin or secretory leukoprotease inhibitor, for α1-antitrypsin deficiency or for general antiprotease protection of the lung in disorders such as cystic fibrosis, emphysema, and bronchitis.
      2. Tissue inhibitor of metalloproteinase—to inhibit collagenase in disorders such as idiopathic pulmonary fibrosis.
      3. Other antiproteases
   B. Antioxidants
      1. Superoxide dismutase (3 forms: Cu$^{++}$/Zn$^{++}$, Mn$^{++}$, and extracellular), catalase, and the enzymes of the glutathione system—for protection against an oxidant burden in disorders such as cystic fibrosis, bronchitis, emphysema, the interstitial lung disorders, cigarette smoking, adult respiratory distress syndrome, the acquired immunodeficiency syndrome.
      2. Other lung disorders in which there is an increased oxidant burden.
   C. Apoprotein components of surfactant for respiratory distress syndrome of the newborn and other disorders in which augmentation of the surfactant system would be efficacious.
   D. Enhancement of local host defense
      1. Interferon—γ, and interleukin-2, for general use.
      2. Defensins and other proteins with antibacterial properties.
      3. Gp 120 and other proteins for the acquired immunodeficiency syndrome.
      4. Other antiviral proteins.
      5. Other proteins with host defense properties.
   E. Mucolytics such as DNase
   F. Cystic fibrosis transmembrane regulator for cystic fibrosis.
   G. Proteins with antitumor properties including, but not limited to tumor necrosis factor -α, interferon - α, interleukin-2 and tumor suppressor proteins such as p53 and the retinoblastoma protein.
   H. Proteins for vaccination for local immunity, for example against viruses, bacteria, fungi, pneumocystis, and other organisms capable of causing lung infection.
   I. Proteins with bronchodilator properties for disorders such as asthma.
   J. Proteins that will block inflammatory cytokines (for example, the soluble form of the tumor necrosis factor—α receptor, or the inhibitor of the interleukin-1 receptor).
   K. Other receptor agonists or antagonists to interfere with pathogenic processes in the lung.
   L. Other proteins for the treatment or prevention of lung disorders.
II. Proteins for local use within the lung (as in "I" above) but for development of animal models of lung disease for the purposes of testing therapeutic agents and for understanding the pathogenesis of human disease.
   A. Proteases that injure the lung such as neutrophil elastase.
   B. Cytokines that recruit inflammatory cells such as interleukin-8 and interleukin 5.
   C. Antiproteases to protect the lung.
   D. Oncogenes to cause lung tumors.
   E. Cytokine and other proteins that will induce animal models of human disease.
III. Proteins for systemic use outside of the lung, where the lung cells are used to produce the protein which then diffuses into the blood. Examples of such proteins include, but are not limited to:
   A. α1-antitrypsin—for α1-antitrypsin deficiency
   B. factor VIII—for hemophilia
   C. other coagulation factors—for bleeding disorders
   D. growth hormone—for growth disorders
   E. insulin—for diabetes
   F. other peptide hormones
   G. other pituitary hormones [adrenal cortical stimulating hormone (ACTH) and thyroid stimulating hormone (TSH) are just two examples]
   H. other lymphokines and cytokines for systemic therapy
   I. interferon γ—for treating granulomatous disease of childhood, and visceral leishmaniasis, and other diseases for augmenting the immune response to other viruses and pathogens.
   J. interferon α—for leukemia and chronic active hepatitis
   K. erythropoietin—for chronic renal failure and other marrow suppressive disorders
   L. other hematologic growth factors—for marrow suppressive disorders
   M. administration e.g., tissue plasminogen activator for prevention of thrombosis in the pulmonary coronary arteries following reperfusion therapy, especially after balloon catheterization, or CD4 for human immunodeficiency virus (HIV) infection, and other recombinant proteins requiring systemic administration, whether short term or long term N. recombinant proteins for other hereditary disorders such as cerebrosidase deficiency and adenosine deaminase deficiency O. receptor agonists or antagonists—for example, for the control of systemic hypertension; interleukin-1 receptor antagonist for septic shock, rheumatoid arthritis and other disorders P. binding proteins for cytokines, lymphokines, and hormones—for example, tumor necrosis factor binding protein (a portion of the tumor necrosis factor receptor) for the treatment of shock and wasting disorders mediated by tumor necrosis factor Q. Proteins for production of vaccines for systemic immunity against infectious agents. One preferred strategy is to put the gene coding for the protein against which immunity is to be developed into the replication deficient adenovirus which is then administered. Examples of such infectious agents include: hepatitis viruses, human immunodeficiency virus, and other viruses that cause human (or animal disease). This strategy may also be used to develop immunity against bacteria, fungi, and other infectious agents.

Next, these replication-deficient adeno-viral vector constructs containing sequence encoding such a desired protein can be used to infect lungs cells. By using a replication deficient adenovirus, the target cells produce the therapeutic protein of interest which is encoded by the construct (note: not derived from integral adenovirus itself), and the process is safe because the virus cannot replicate in the target cells.

The particular formulation employed will be selected according to conventional knowledge depending on the properties of the protein or polypeptide and the desired site of action to ensure bioavailability of the active ingredients, i.e., the extent to which the drug reaches its site of action or a biological fluid from which the drug has access to its site of action. Dosages for a given host can be determined using conventional considerations, e.g., by customary comparison of the differential activities of the subject preparations and a known appropriate, conventional pharmacological protocol.

Suitable pharmaceutically acceptable carriers are well known in the art. Examples of typical carriers include saline, buffered saline and other salts, liposomes, and surfactants. The adenovirus may also be lyophilized and administered in the forms of a powder. Taking appropriate precautions not to kill the replication-deficient adenovirus, the preparations can be sterilized and if desired mixed with auxiliary agents, e.g., lubricants, preservatives, stabilizers, wetting agents, emulsifiers, salts for influencing osmotic pressure, buffers, and the like that do not deleteriously react with the active virus. They also can be combined where desired with other biologically active agents, e.g., antisense DNA or mRNA.

The actual preferred amounts of replication-deficient adenovirus administered in a specific case will vary according with the specific protein or polypeptide being utilized, the particular compositions formulated, the mode of application, and the particular situs and organism being treated.

The dosages of the biologically active compounds administered according to this invention are generally known in the art. Generally, the preparations of this invention are dispensed in dosage unit form comprising $10^6$–$10^{14}$ pfu/ml of the replication-deficient adenovirus in a pharmaceutically acceptable carrier per unit dosage, preferably about $10^{10}$–$10^{13}$ pfu/ml. The adenovirus can be administered by local installation through a tube such as a flexible bronchoscope, by aerosolization (preferably, in a droplet or powder form), or by other techniques known to one skilled in the art (U.S. application Ser. No. 07/504,047 is hereby incorporated by reference).

The use of proteins and polypeptides as therapeutic agents is greatly expanded according to the present invention by providing a means for delivering effective amounts of biologically active protein to the lung of a recipient. The preparations of this invention are suitably administered to animals, which include but are not limited to mammals (including humans), fish, and avians. The preparations are preferably administered to livestock (including cattle, horses, swine, sheep, goats, etc.), household pets (cats, dogs, canaries, parakeets, etc.) fish (especially in an aquarium or acquaculture environment, e.g., tropical fish, goldfish and other ornamental carp, catfish, trout, salmon, etc.) and avians, especially poultry such as chickens, ducks, geese, etc.

This approach provides a means of administering recombinant proteins to these animals for general therapeutic purposes. The uses for animals include the production of immunity (e.g., vaccination) against infectious agents. Also included would be proteins to treat disorders of animals, fish, etc. This strategy may also be used to deliver genes to animals to use the animal to produce proteins for humans use e.g., after purification from biologic fluids of the animal.

In another aspect, this embodiment is useful in the treatment of disorders in which proteins or polypeptides are useful therapeutic agents, particularly when the gene coding the protein of interest is derived from the species being treated, or with sequences which are closely homologous to prevent immune reactions.

A particularly important aspect of the present invention involves the use of replication-deficient adenovirus as a delivery system for chemotherapeutic agents, including antisense compounds, especially for use in cancer chemotherapy. Briefly, use with antisense compounds for use against tumor cells in the lung involves selecting mRNA as the primary drug target, with either another mRNA molecule or a synthetic oligo deoxynucleotide having the complementary base sequence to the mRNA forming a hybrid duplex by hydrogen-bonded base pairing. This hybridization can prevent expression of the target mRNA's protein product, a process called "translation arrest". Inhibition of mRNA is more efficient than inhibition of an enzyme active site because a single mRNA molecule gives rise to multiple protein copies. Thus, the selective inhibition of expression of a gene product required for cellular function yields the elusive but highly desired goal of chemotherapy: selective cell death. Such approaches are known in the literature, e.g., see J. S. Cohen, "Antisense Oligonucleotides as an Approach Toward Anti-Aids Therapy" at pages 195–224 in *Design of Anti-Aids Drugs*, E. declerg (Ed), Elsevier Publishing Co. (1990); and S. L. Loke, et al. *Current Topics in Microbiology and Immunology* 141: 282–289 (1988).

The present invention is described in further detail in the following non-limiting Examples.

EXAMPLES

To demonstrate the feasibility of the invention, two replication deficient recombinant adenovirus constructs (FIGS. 1 and 6) were used to transfer the sequences coding for human α1-antitrypsin and a cystic fibrosis transmembrane conductance regulator protein to the lung.

The following protocols and experimental details are referenced in the Examples that follow:

Ad-α1AT Vector construction and propagation (as presented in FIG. 1). The recombinant vector Ad-α1AT is constructed by deleting the majority of the E3 region and 2.6 mu from the left end of Ad5 and adding to the left end the α1AT expression cassette from the plasmid pMLP-α1AT which contains regulatory sequences and a recombinant human α1AT gene (Gilardi, P. et al. (1990) FEBS Lett. 267, 60). To construct the recombinant viral vector Ad-α1AT, the expression cassette was ligated with ClaI-precut Ad-dl327 DNA (B. Thimmappaya (1982) Cell 31, 543) (to remove a portion of the Ela region from Ad-dl327). The recombinant adenovirus DNA was transfected into the 293 cell line (Graham, F. L. et al. (1977) J. Gen. Virol. 35, 59; Graham, F. L. and Van Der Ed, A. J. (1973) Virology 52, 456) where it was replicated, encapsidated into an infectious virus, and isolated by plaque purification. Individual plaques were amplified by propagation in 293 cells and viral DNA extracted (Hirt, B. (1967) J. Mol. Biol. 26, 365). The intactness of the DNA of the recombinant virus was confirmed before use by restriction fragment analysis and Southern (DNA) blot. Stocks of Ad-α1AT and the Ad5 Ela deletion mutant Ad-dl312 were propagated and titered in 293 cells (Graham, F. L. et al. (1977) J. Gen. Virol. 35, 59). The virus was released from infected cells 36 hours post-infection by 5 cycles of freeze/thawing. For some in vivo experiments Ad-α1AT was further purified with CsCl (Graham, F. L. and Van Der Ed, A. J. (1973) Virology 52, 456).

Expression of human α1AT Cotton rats were anesthetized (methoxyflurane inhalation), exposed the trachea and lungs through a midline thoracic incision, and perfused the pulmonary vasculature perfused with LHC-8 medium (Biofluids) to remove blood. The trachea was transected, and the tracheobronchial epithelial cells (to the second order bronchi) were recovered with a cytologic brush. The epithelial cells were gently pelleted (300 g, 8 min, 23°), resuspended in LHC-8 medium, plated on fibronectin-collagen-coated plates (Lechner, J. F. et al. (1982) In Vitro 18, 633), and infected with $2 \times 10^7$ plaque forming units (PFU) of Ad-α1AT in LHC-8 medium or, as a control, exposed to only LHC-8 medium. After 1 day, expression of α1AT mRNA transcripts was evaluated in cytocentrifuge preparations by the technique of in situ hybridization (Harper, M. E. (1986) Proc. Natl. Acad. Sci. U.S.A. 83, 772; Bernaudin, J.-F. et al. (1988) J. Immunol. 140, 3822) with $^{35}$S-labeled sense and antisense RNA probes ($1.2 \times 10^5$ cpm/μl) prepared in pGEM-3Z (Promega). After hybridization, the cells were evaluated by autoradiography for 1 week and counterstained with hematoxylin and eosin (HE). After 1 day, the cells were labeled with [$^{35}$S]methionine (500 μCi/ml; 24 hours, 37°) and the supernatant evaluated by immunoprecipitation with goat antibodies to human α1AT (Cappel), sodium dodecyl sulfate (SDS)-polyacrylamide gel electrophoresis and autoradiography (Mornex, J.-F. et al. (1986) J. Clin. Invest. 77, 1952).

Expression of human α1AT mRNA transcripts and synthesis and secretion of human α1AT. Cotton rats were anesthetized, and Ad-α1AT was diluted in 300 μl PBS to $10^8$ PFU/ml and instilled into the trachea. Controls included 300 μl of PBS or 300 μl of PBS with Ad-dl312 at $10^8$ PFU/ml. After 1 to 7 days, lungs were exposed, lavaged, and the pulmonary vasculature perfused with methionine-free LHC-8 medium.

Total RNA was extracted (Chirgwin, J. M. et al. (1979) Biochemistry 18, 5294), treated with an excess amount of DNAse (RQ1 RNase-Free DNase, Promega), converted the RNA to cDNA by standard techniques, and amplified by polymerase chain reaction (PCR) for 25 cycles (Saiki, R. K. et al. (1988) Science 239, 487) with an adenoviral-specific primer in the tripartite leader sequences (FIG. 1) and a human α1AT exon III-specific antisense primer. To eliminate the possibility of contaminating viral DNA amplification, each DNase-treated RNA sample was also used as a PCR template without conversion to cDNA. PCR products were evaluated by agarose gel electrophoresis followed by Southern hybridization with a human α1AT cDNA probe that was $^{32}$P-labeled by random priming (Church, G. M. and Gilbert, W. (1984) Proc. Natl. Acad. Sci. U.S.A. 81, 1991; Feinberg, A. P. and Vogelstein, B. (1983) Anal. Biochem. 132, 6).

At various times after infection, the lungs were minced, incubated for 1 hour in methionine-free LHC-8 medium (37°), and then incubated for 24 hours in medium with ($^{35}$S)-methionine (1 ml medium/150 mg tissue; 500 μCi/ml). The supernatant was then evaluated by immunoprecipitation with a rabbit antibody to human α1AT (Boehringer Mannheim), SDS-polyacrylamide gels, and autoradiography. Trichloroacetic acid-precipitable radioactivity was evaluated by immunoprecipitation. The ability of the synthesized human α1AT to inhibit its natural substrate, NE, was evaluated by incubating the supernatant with various dilutions of active NE (30 min, 23°) before immunoprecipitation.

In situ hybridization evaluation of cotton rat lung infected in vivo with Ad-α1AT. Cotton rats were infected in vivo as described above, with 300 μl of PBS alone or with 300 μl of Ad-α1AT diluted to $10^8$ to $10^{10}$ PFU/ml in PBS. After 3 days, the lungs were exposed, blood was removed by cardiac puncture, and the lungs were lavaged. The trachea and pulmonary vasculature were perfused with 4% paraformaldehyde (PFA; Fluka Chemical Corp.); the lungs were resected, fixed in 4% PFA, and frozen. Cryostat sections (7 to 10 μm) were serially treated with 0.2M HCl and proteinase K (1 μg/ml) immediately prior to hybridization and evaluated with $^{35}$S-labeled antisense and sense RNA probes as described above. As far as possible, serial sections were used for the antisense and sense probes.

Figure 2:
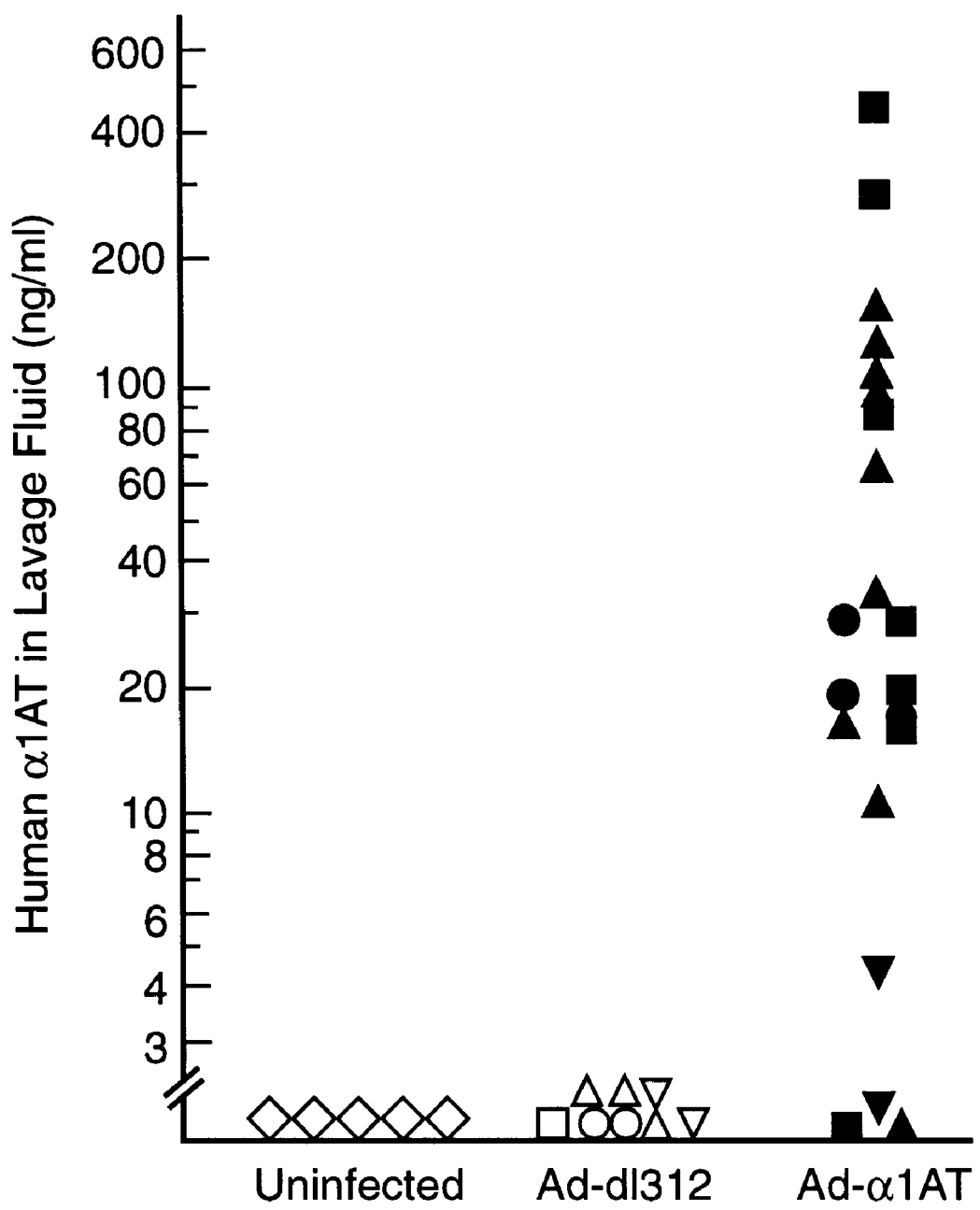
FIG. 2. The amount of human α1AT in the respiratory epithelial lining fluid (ELF) of cotton rats after in vivo infection with Ad-α1AT. Each symbol represents the mean value of an individual animal. All uninfected animals are shown as ◇. For the control virus Ad-dl312 and for Ad-α1AT, the different symbols refer to the time point after infection (1 day o,·2 days ∆,▲; 3 days □,■; 7 days ▲,▽). No α1AT was detected by ELISA in the viral preparations used for infection.

Amount of human α1AT in the respiratory epithelial lining fluid (ELF) of cotton rats after in vivo infection with Ad-α1AT (as presented in FIG. 2). Animals were infected intratracheally with CsCl purified Ad-α1AT ($10^8$ to $10^{10}$ PFU/ml) as described above; controls included uninfected animals and those infected with a similar titer of Ad-dl1312. From 1 to 7 days after infection, ELF was obtained by lavage of the lungs with 2 ml of PBS. Lavage fluid was clarified (700 g, 20 min) and the concentration of human α1AT quantified (in quadruplicate) with a human α1AT specific enzyme-linked immunoassay (ELISA) (Michalski, J. P. (1985) J. Immunol. Methods 83, 101) with a sensitivity of ≧3 ng/ml.

Cell Cultures. The transformed human embryonic kidney cell line 293 [American Type Culture Collection (ATCC) CRL 1573 (Graham, F. L. (1986) J. Virol. 57, 267; Ballay, A. et al. (1985) EMBO J. 4, 3861)] was grown in Improved minimal essential medium (Biofluids Inc.) containing 10% fetal bovine serum (FBS), 2 mN glutamine, 50 units/ml penicillin, and 50 μg/ml streptomycin. CFPAC-1 cells, originally derived from a pancreatic adeno-carcinoma of an individual homozygous for the common F508 CF mutation (Schoumacher, R. A. et al. (1990) Proc. Natl. Acad. Sci. USA 87:4012–4016), were grown in Dulbecco's modified Eagle's medium (DMEM, Biofluids) with supplements as above. The human colon adenocarcinoma cell line T84 (ATCC CCL 248) was cultured as for CFPAC-1 cells, except with 5% FBS.

Construction of the Recombinant Adenoviral Vector Ad-CFTR. The recombinant adenovirus Ad-CFTR was constructed from the adenovirus type 5 (Ad 5) deletion mutant, Ad-dl324 (Thimmappaya, B. et al. (1982) Cell 31:543–551) and a plasmid (pTG5955) containing the 5' inverted terminal repeat, origin of replication, encapsidation signal, and Ela enhancer (all from Ad 5); the major late promoter and the majority of the tripartite leader sequence cDNA (both from Ad 2); the 4.5 kb human CFTR cDNA including the entire protein coding sequence; the SV40 early polyadenylation signal; and the Ad 5 sequences from nucleotide positions 3329 to 6241. Plasmid pTG5955 was linearized by ClaI cleavage and cotransfected with ClaI-cut Ad-dl324 DNA into 293 cells to allow homologous recombination to occur. Recombinant adenoviral DNA was then replicated and encapsidated into infectious virions which were screened by plaque purification. Individual plaques were amplified in 293 cells, viral DNA was isolated (Hirt, B. (1967) J. Mol. Biol. 26:365–369), and recombinant adenovirus plaques containing the human CFTR CDNA (Ad-CFTR) were identified by restriction cleavage and Southern analysis. Ad-CFTR and the control viruses Ad-α1AT (Rosenfeld, M. R. et al. (1991a) Science 252:431–434) and the Ela deletion virus Ad-dl312 (Jones, N. and Shenk, T. (1979) Cell 17, 683) were propagated in 293 cells and recovered 36 hr after infection by 5 cycles of freeze/thawing. All viral preparations were purified by isopycnic cesium chloride (CsCl) density centrifugation (Graham, F. L. and Van Der Eb, A. J. (1973) Virology 52:456–467), dialysed and stored in 10 mM Tris-HCL, pH 7.4, 1 mM MgCl, 10% glycerol at −70° prior to use. Titers of the viral stocks were determined by plaque assay using 293 cells (Graham, F. L. and Van Der Eb, A. J. (1973) Virology 52:456–467; Graham, F. L. et al. (1977) J. Gen. Virol. 36:59–72).

In Vitro and In Vivo Infection with Ad-CFTR. For in vitro infection, the cells were trypsinized, counted, seeded [10 cm plates ($4.5 \times 10^6$ cells/plate) for evaluation of CFTR mRNA or synthesis of CFTR protein; 6 cm plates ($5.0 \times 10^5$ cells/plate) for evaluation of Cl⁻ secretion in response to forskolin] and infected with Ad-CFTR, Ad-dl312, or Ad-α1AT (200 plaque forming units (PFU) per cell for CFPAC-1 cells; 50 PFU per cell for 293 cells). After 18 to 24 hr (for 293 cells) or 48 hr (for CFPAC-1 cells), cells were evaluated for CFTR mRNA, synthesis of CFTR protein, and Cl⁻ secretion in response to forskolin (see below). For in vivo studies, cotton rats (Sigmodon hispidus) were anesthetized by methoxyfluorane inhalation. The trachea was exposed by anterior midline incision and $10^{10}$ PFU of Ad-CFTR or Ad-dl312 were injected into the trachea in a total volume of 300 μl of phosphate buffered saline, pH 7.4 (PBS). An equal volume of PBS (with glycerol at the concentration contained in the viral preparations used for the infection) was injected in other cotton rats as an additional negative control.

Analysis of CFTR mRNA Expression by In Situ Hybridization. Cotton rat lungs and trachea were isolated as described above. After blood was removed by cardiac puncture, the lungs were fixed with 4% paraformaldehyde (PFA, Fluka) infused into the trachea and pulmonary artery and cyrostat sections (7 to 10 μm) were cut and stored frozen (−70°) until use. Immediately prior to hybridization, cryostat sections were sequentially treated with 0.2 M HCl and 1 μg/ml proteinase K. Three different sets of human CFTR ³⁵S-labeled sense and antisense cRNA probes were synthesized in vitro from plasmid transcription vectors (pGEM, Promega) with [³⁵S]UTP (1 mCi, 800 Ci/mmol, SP6/T7 grade; Amersham) by standard techniques. Each PGEM CFTR vector contained a different region of human CFTR cDNA (exons 1–5, 9–13, or 21–24). These probes were combined, hydrolyzed and the lung tissue sections were then hybridized (12 hr, 50°) with the labeled cRNA probes ($1.2 \times 10^5$ dpm/μl). Lung tissue sections were then washed, treated with RNase A (50 μg/ml, Sigma), washed, dehydrated, and evaluated by autoradiography (10 d) and counterstained with hemotoxylin and eosin (Harper, M. E. et al. (1986) Proc. Natl. Acad. Sci. U.S.A. 83:772–776; Bernaudin, J-F. et al. (1988) J. Immunol. 140, 3822–3829; Rosenfeld, M. R. et al. (1991a) Science 252:431–434).

Northern Analysis of CFTR mRNA Transcripts. For in vitro infection experiments, total RNA was isolated from 293 cells or CFPAC-1 cells (at 20 and 48 hr after adenoviral vector infection, respectively) or as a control from uninfected sub-confluent T84 cells, using the guanidine thiocyanate-CsCl technique (Chirgwin, J. M. et al. (1979) Biochemistry, 18:5294–5299). For in vivo studies, cotton rats were evaluated two d to 6 wk after infection and the lungs were isolated as described above. Following exanguination by cardiac puncture, the lungs were lavaged twice, the pulmonary artery was perfused with PBS and the lungs and trachea were resected, minced and total lung RNA was extracted (Chirgwin, J. M. et al. (1979) Biochemistry, 18:5294–5299; Rosenfeld, M. R. et al. (1991a) Science 252:431–434).

RNA was subjected to formaldehyde-agarose gel electrophoresis, transferred to a nylon membrane (Nytran, Scleicher & Schuell), hybridized with a ³²P-labeled, 4.5 kb CFTR cDNA probe prepared by random priming and evaluated by autoradiography as previously described (Yoshimura, K. et al. (1991) J. Biol. Chem. 266:9140–9144). As a control, the same membranes were subsequently hybridized with either a human β-actin cDNA probe [pHFβA-1, for cultured human cells (Gunning, P. et al. (1983) Mol. Cell. Biol. 3(5):787–795)] or a rat glutaldehyde-3-phosphate dehydrogenase (GAPDH) cDNA probe [for rat lung RNA (Tso, J. Y. et al. (1985) Nucl. Acids. Res. 13:2485–2502)].

Detection of CFTR mRNA Transcripts Using the Polymerase Chain Reaction. Ad-CFTR-directed CFTR mRNA transcripts were evaluated in rat lung RNA (prepared as above) after conversion to cDNA, PCR amplification and Southern hybridization analysis. RNA was first treated with DNase (10 units/μg RNA; RNase-free RQ1 DNase, Promega) to eliminate possible residual viral DNA. RNA was then converted to cDNA by standard techniques using Moloney murine leukemia virus reverse transcriptase (RT) with random hexanucleotide primers (Roth, M. J. et al. (1985) J. Biol. Chem. 260:9326–9335) and amplified by PCR (25 cycles) and Taq DNA polymerase [Perkin Elmer Cetus; (Saiki, R. K. et al. (1988) Science 239:47=87–491)]. To insure that Ad-CFTR driven transcripts were specifically evaluated and that the 5' and 3' portions of the mRNA transcripts were present, two separate primers-pairs were used: a 5' primer pair to detect the 5' end of Ad-CFTR mRNA transcripts consisting of an adenoviral-specific sense primer in the tripartite leader sequence (VAD-5; 5'-AGCTGTTGGGGCTCGCGGTTGAGG-3'; SEQ ID NO:1) and a human CFTR-specific antisense primer in CFTR exon 5 (HCF60; 5'-CATCA-AATTTGTTCAGGTTGTTGG-3'; SEQ ID NO:2); and a 3'primer pair to evaluate the 3' end of Ad-CFTR mRNA transcripts consisting of a human CFTR-specific sense primer in CFTR exon 21 (HCF12; 5'-AGTGGAGTGATCAAGAAATATGG-3'; SEQ ID NO:3) and an SV40 viral-specific primer in the SV40 early mRNA polyadenylation signal sequence (SVPOLYA; 5'-GTAACCATTATAAGCTGCAATAAAC-3'; SEQ ID NO:4; Fiers, W. et al. (1978) Nature 273:113–120). As a control, rat GAPDH transcripts corresponding to amino acid residues 126 to 300 were amplified under similar conditions using GAPDH transcript-specific primers [(GAPDH-1; 5'-AATGCATCCTGCACCACCAACTGC-3'; SEQ ID NO:5) and (GAPDH-2; 5'-GGAGGCCATGTAGGCCATGAGGTC-3'; SEQ ID NO:6; Tso, J. Y. et al. (1985) Nucl. Acids Res. 13:2485–2502)]. Each DNase-treated RNA sample was also used as a PCR template in parallel without conversion to cDNA to eliminate the possibility that amplification of potentially contaminating viral DNA occurred. PCR amplification products were evaluated by agarose gel electrophoresis followed by Southern hybridization using nested or internal $^{32}$P-labeled human CFTR CDNA probes [a 462 bp PvuII-XbaI fragment spanning exons 2 to 5 (Riordan, J. R. et l. (1989) Science 245:1066–1073) for the 5' region amplificaton products, or a 200 bp fragment spanning exons 22 to 23 (Riordan, J. R. et al. (1989) Science 245:1066–1073;Yoshimura, K. et al. (1991) J. Biol. Chem. 266:9140–9144; Trapnell, B. C. et al. (1991a), J. Biol. Chem. 266:10319–10323) for the 3' region amplification products]; or an internal rat GAPDH cDNA probe [a 281 bp BanII fragment within the amplified GAPDH transcript region described above (Tso, J. Y. et al. (1985) Nucl. Acids. Res. 13:2485–2502)].

In Vitro Evaluation of the Function of Ad-CFTR-Derived Human CFTR. In vitro synthesis of human CFTR was evaluated in 293 and CFPAC-1 cells after Ad-CFTR infection. Cells were incubated in labeling medium [methionine-free LHC-8 medium (Biofluids) containing [$^{35}$S]methionine (500 μCi/ml; 1000 Ci/mmol, New England Nuclear] during the entire infection period. After infection (24 h for 293 cells; 48 hr infection for CFPAC-1 cells) cells were washed twice in PBS, and solubilized at 4° in lysis buffer [PBS containing 10 mM ethylen-ediaminetetraacetate, 1% Triton X-100, 0.5% sodium deoxycholate, 200 μg/ml aprotinin, 100 μg/ml leupeptin (both from Boehringer Mannheim), and 2 mM phenymethylsulfonyl fluoride, (Sigma)]. The cell lysate was frozen (–70° for at least 30 min), thawed and clarified by centrifugation (12,000 g, 4°, 30 min); for each 293 cell sample $3 \times 10^6$ dpm and for each CFPAC-1 cell sample $30 \times 10^6$ dpm total trichloracetic acid precipitable radioactivity was used to evaluate $^{35}$S-labeled human CFTR by immuno-precipitation with a mouse anti-human CFTR monoclonal antibody (Genzyme), followed by sodium dodecyl sulfate (SDS)-polyacrylamide gel electrophoresis and fluororadiography (Mornex, J.-F. et al. (1986) J. Clin. Invest. 77, 1952; Rosenfeld, M. R. et al. (1991a) Science 252:431–434.

To demonstrate that the Ad-CFTR vector was capable of directing the expression of functional CFTR protein, forskolin-stimulated Cl$^-$secretion was evaluated in cells that do not normally exhibit cAMP-mediated Cl- secretion (293 cells) or in human epithelial cells derived from an individual with CF [CFPAC-1 cells, a cell line with the homozygous expression of the F508 CF mutation (Schoumacher, R. A. et al. (1990) Proc. Natl. Acad. Sci. USA 87:4012–4016)]. To accomplish this, at 18 hr (293 cells) or 48 hr (CFPAC-1 cells) after infection with Ad-CFTR, Cl$^-$efflux was evaluated (Trapnell, B. C. et al. (1991a), J. Biol. Chem. 266:10319–10323). Briefly, monolayers of 293 or CFPAC-1 cells were washed twice with Ringer's lactate and loaded with $^{36}$Cl$^-$ (2.5 μCi/ml; >3 mci/gram Cl, Amersham; 2 hours, 37°) and then washed rapidly with 3 ml aliquots (×6) of Ringer's lactate buffer. $^{36}$Cl$^-$ efflux was measured by sequentially removing and replacing buffer (0.9 ml aliquots) at various time intervals for up to 7.5 min. The cells were then removed from the dish with 0.9 ml of 0.25% trypsin (Biofluids) and the amount of $^{36}$Cl$^-$ in the efflux aliquots and cells determined by liquid scintillation counting. The total radioactivity loaded into cells was calculated from the sum of the individual efflux time points plus that remaining in cells at the end of the sampling period and the Cl$^-$ efflux data plotted for each time point as $^{36}$Cl$^-$ remaining in cells as a percentage of total $^{36}$Cl$^-$ initially loaded into cells. Forskolin stimulated Cl$^-$ secretion was evaluated by adding 13 μM forskolin (Sigma, St. Louis, Mo.), to the sampling buffer used for collection of the efflux samples.

EXAMPLE 1

Adenovirus-mediated Transfer of a Recombinant α1-Antitrypsin Gene to the Lung Epithelium in Vivo The adenovirus (Ad) major late promoter (MLP) was linked to a recombinant human α1-antitrypsin (α1AT) gene (Crystal, R. G. (1990) J. Clin. Invest. 85, 1343) and was incorporated into a replication-deficient recombinant (FIG. 1) (Straus, S. E. (1984) In: The Adnoviruses (H. S. Gingsberg Ed.) Plenan Press, New York and London, pp. 451–496; Gilardi, P. et al. (1990) FEBS Lett. 267, 60). The vector has a deletion of a portion of the E3 region (that permits encapsidation of the recombinant genome containing the exogenous gene) and a portion of the viral E1a coding sequence (that impairs viral replication), but contains an insert of an α1AT expression cassette (FIG. 1) (Gilardi, P. et al. (1990) FEBS Lett. 267, 60; Courtney, M. et al. (1984) Proc. Natl. Acad. Sci. U.S.A. 81, 669). After packaging into an infectious, but replication deficient virus, Ad-α1AT is capable of directing the synthesis of human α1AT in Chinese hamster ovary (CHO) and human cervical carcinoma (HeLa) cell lines (Gilardi, P. et al. (1990) FEBS Lett. 267, 60).

Tracheobronchial epithelial cells were obtained by brushing the epithelial surface of the tracheobronchial tree from the lungs of the cotton rat [Sigmodon hispidus, an experimental animal used to evaluate the pathogenesis of respiratory tract infections caused by human adenoviruses (Ginsberg, H. S. et al. (1989) Proc. Natl. Acad. Sci. U.S.A. 86, 3823)] (FIG. 2). The freshly removed cells infected in vitro with Ad-α1AT expressed human α1AT mRNA transcripts, as demonstrated by in situ hybridization with a $^{35}$S-labeled antisense human α1AT RNA probe (FIG. 2). In contrast, no human α1AT mRNA transcripts were observed in uninfected, freshly isolated tracheobronchial epithelial cells. Human α1AT mRNA transcripts in the infected cells were capable of directing the synthesis and secretion of human α1AT as shown by biosynthetic labeling and immunoprecipitation with a specific antibody to human α1AT.

The newly synthesized, secreted α1AT was human α1AT, as shown by the fact that human α1AT but not by cotton rat serum, blocked the antibody to human α1AT.

Figure 3:
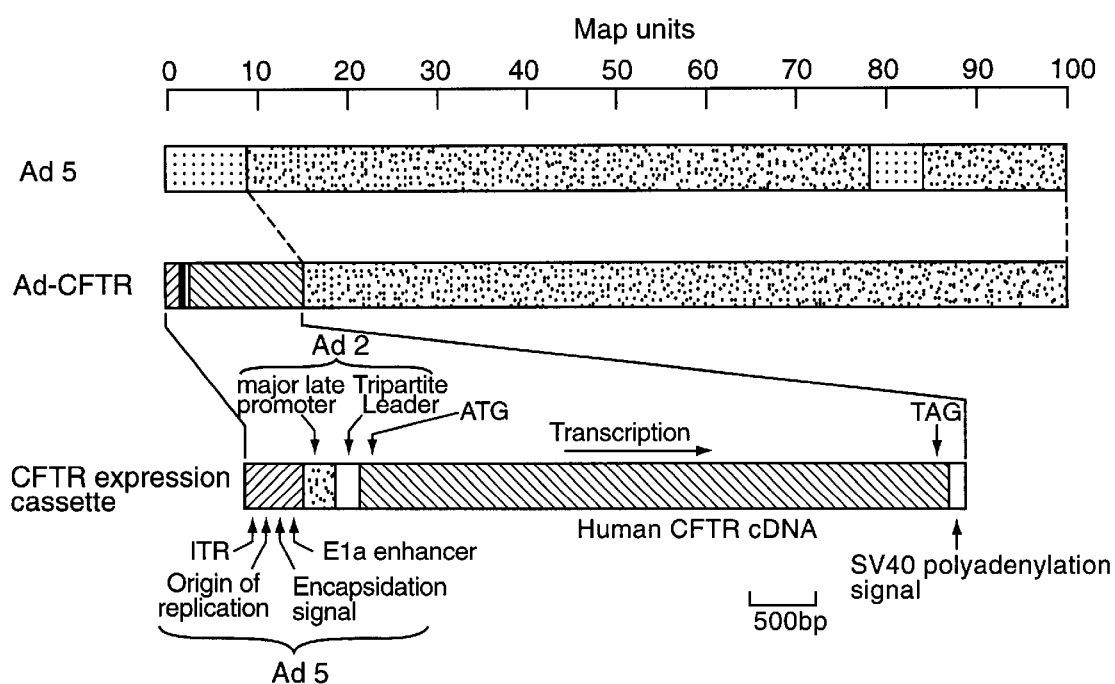
FIG. 3. Schematic of the recombinant adenoviral vector Ad-CFTR. Shown are the adenovirus type 5 (Ad 5) genome, the recombinant adenoviral DNA containing the human CFTR cDNA (Ad-CFTR) and a detailed enlargement of the CFTR expression cassette. Ad 5 DNA is divided into 100 map units (mu) [360 base pairs (bp)/mu]. Stippled segments of Ad 5 indicate deletions of the majority of the E1 region (0–9.2 mu) and E3 (78.4–84.3 mu) which were removed in the construction of Ad-CFTR to allow room for insertion of exogenous, non-viral DNA. The CFTR expression cassette includes: the 5' inverted terminal repeat (ITR), origin of replication, encapsidation signal, and E1a enhancer (all from Ad 5); the major late promoter and a copy of the tripartite leader sequence cDNA (both from Ad 2); the entire 4.5 kb protein coding sequence of the human CFTR cDNA [from nucleotide 123 to 4587 (see Riordan, J. R. et al. (1989) Science 245, 1066, for sequence numbering)]; and the SV40 early mRNA polyadenylation signal. The CFTR protein translation start (ATG) and stop (TAG) signals are indicated.

Ad-α1AT transferred the recombinant α1AT gene to the cotton rat lung in vivo (FIG. 3). Human α1AT transcripts were observed in the lungs two days after intratracheal instillation of Ad-α1AT, but not in lungs of animals that received only phosphate-buffered saline (PBS), or in lungs of animals that received the Ad5 E1a-deletion mutant, Ad-dl312 (Jones, N. and Shenk, T. (1979) Cell 17, 683). Biosynthetic labeling and immuno-precipitation of extracellular protein from lung fragments of lung removed from infected animals demonstrated that de novo synthesis and secretion of human α1AT also occurred had been infected in vivo; this was not observed in uninfected animals or animals infected with Ad-dl312. The de novo expression of the human α1AT protein lasted at least 1 week and the secreted human α1AT was functional, as shown by its ability to form a complex with its natural target, human neutrophil elastase (NE).

Two lines of evidence demonstrated that the infection of the cotton rat lung with Ad-α1AT took place in vivo, and was the result of virus carried over into the in vitro biosynthetic analysis. First, immediate evaluation of lung tissue removed 2 and 3 days after in vivo infection with Ad-α1AT revealed human α1AT mRNA transcripts. Second, evaluation of the respiratory epithelial lining fluid of cotton rats 3 days after infection with Ad-α1AT showed no evidence of infectious virus capable of directing the biosynthesis of human α1AT, as evidenced by exposure of the 293 cell line to epithelial lining fluid and $^{35}$S-labeled-methionine, followed by immunoprecipitation analysis in a manner identical to that used for the analysis of the α1AT biosynthesis by the lung fragments.

Evaluation of the cotton rat lung by in situ hybridization with antisense and sense α1AT RNA probes revealed human α1AT mRNA transcripts in lung cells of animals infected with Ad-α1AT, but not in those of uninfected animals. The expression of human α1AT mRNA transcripts was patchy, as could be from the method of intratracheal administration of Ad-α1AT; more uniform expression should be achieved by modifications of vector delivery methods such as by aerosol. Consistent with the observation that cotton rat respiratory epithelial cells were easily infected in vitro, most of the transcripts were in epithelial cells; the available methodologies do not permit an accurate assessment of the distribution of expression among the multitude of epithelial cell types in the lung. Occasional grains were observed within interstitial cells.

Evaluation of the fluid lining the epithelial surface of the lungs with a human α1AT-specific enzyme-linked immunosorbent assay (ELISA) demonstrated the presence of human α1AT in animals infected with AD-α1AT, but not in those infected with the deletion mutant virus AD-dl312 or in uninfected animals (FIG. 3). Human α1AT could be detected at all the periods evaluated (days 1 to 7 after Ad-α1AT infection). No adverse effects were observed in the animals at any time after infection with either Ad-dl312 or Ad-α1AT. Because the methods available for administration of Ad-α1AT to the animals result in variable delivery and retention of the vector, it is difficult to make quantitative animal-to-animals comparisons. Thus, the time course for α1AT expression cannot be accurately determined at this time, although the de novo biosynthesis data demonstrate that the lung is still actively synthesizing human α1AT at day 7).

EXAMPLE 2

Construction and Expression of the Recombinant Adenoviral Vector Ad-CFTR

Ad-CFTR, a replication-deficient recombinant adenovirus containing the human CFTR protein coding sequence CDNA, was constructed using a modified type 5 adenoviral (Ad 5) genome (FIG. 3). The majority of the E3 region [78.4 to 84.3 map units (mu)] was deleted to provide space for insertion of a cassette containing the 4.5 kb coding sequence of the human CFTR gene (Thimmappaya, B. et al. (1982) Cell 31:543–551; Riordan, J. R. et al. (1989) Science 245:1066–1073. The left end of the viral genome [0 to 9.2 mu (the Ela and the majority of the Elb region)] was deleted and replaced by the CFTR expression cassette which contained essential viral cis-acting elements including the inverted terminal repeat (ITR), origin of replication, and the encapsidation signal, as well as the Ela enhancer, but not the Ela structural gene, a substitution that eliminates autonomous replication of the recombinant vector by removal of the Ela function. The E1a enhancer was followed by the Ad 2 major late promoter and a 4.5 kb CFTR cDNA [nucleotides 123–4587 (see Riordan, J. R. et al. (1989) Science 245:1066–1073 for sequence numbering)]. Ad-CFTR was replicated in the permissive cell line 293 [a human kidney cell line containing a functional Ela gene that provides a trans-acting Ela protein (Graham, F. L. et al. (1977) J. Gen. Virol. 36:59–72)] and high-titer, infectious Ad-CFTR viral stocks were prepared. Within the Ad-CFTR expression cassette, the adenoviral type 2 (Ad 2) major late promoter (MLP) was used to drive transcription of human CFTR mRNA sequences. The majority of the Ad 2 tripartite leader sequence cDNA was included to increase the translation efficiency of CFTR protein expression (Mansour, S. L. et al. (1986) Mol. Cell. Biol. 6:2684–2694.

Following intratracheal administration of Ad-CFTR in cotton rats in vivo, the presence of human CFTR mRNA transcripts could be detected in bronchial epithelium by in situ hybridization analysis using human CFTR cRNA probes Control animals not infected with Ad-CFTR did not show hybridization with the antisense probes. In contrast, hybridization of the antisense probes demonstrated expression of human CFTR mRNA sequences diffusely throughout the epithelium of the airways of animals infected with Ad-CFTR. As a further control, sense probes did not show hybridization in bronchial tissues from uninfected or Ad-CFTR infected cotton rats. The absence of hybridization with the sense probes in the lung of Ad-CFTR-infected animals also indicated that any residual Ad-CFTR DNA that might be present in the tissue was not detectable by the methods utilized.

Ad-CFTR directed expression of human CFTR mRNA transcripts both in vitro and in vivo. As previously observed, northern analysis of T84 human colon carcinoma cells demonstrated 6.5 kb CFTR mRNA transcripts (Riordan, J. R. et al. (1989) Science 245:1066–1073; Drumm, M. L. et al. (1990) Cell 62:1227–1233; Kartner, N. et al. (1991) Cell 64:681–691; Yoshimura, K. et al. (1991) J. Biol. Chem. 266:9140–9144; Trapnell, B. C. et al. (1991a), J. Biol. Chem. 266:10319–10323 while uninfected 293 or CFPAC-1 cells did not contain detectable CFTR mRNA transcripts using the 4.5 kb human CFTR probe. Similarly, in vitro infection of 293 cells or CFPAC-1 cells by the control virus Ad-dl312 [Ad 5 with a deletion of the Ela region (1.5 to 4.5 mu; Jones, N. and Shenk, T. (1979) Cell 17:683–689)] which does not contain the CFTR cDNA did not demonstrate detectable CFTR transcripts. In contrast, 5.2 kb transcripts (the expected size of Ad-CFTR-directed human mRNA transcripts) were observed after in vitro Ad-CFTR infection of 293 cells or CFPAC-l cells. The levels of human β-actin transcripts were similar in all samples. Importantly, Ad-CFTR-directed human CFTR mRNA transcripts of a size similar to that directed by Ad-CFTR in cultured cells, were observed in total lung RNA 48 hr after in vivo infection of cotton rats by intratracheal instillation of Ad-CFTR, but not in uninfected animals. Levels of rat glyceraldehyde-3-phosphate dehydrogenase transcripts were similar for both samples.

Figure 4:
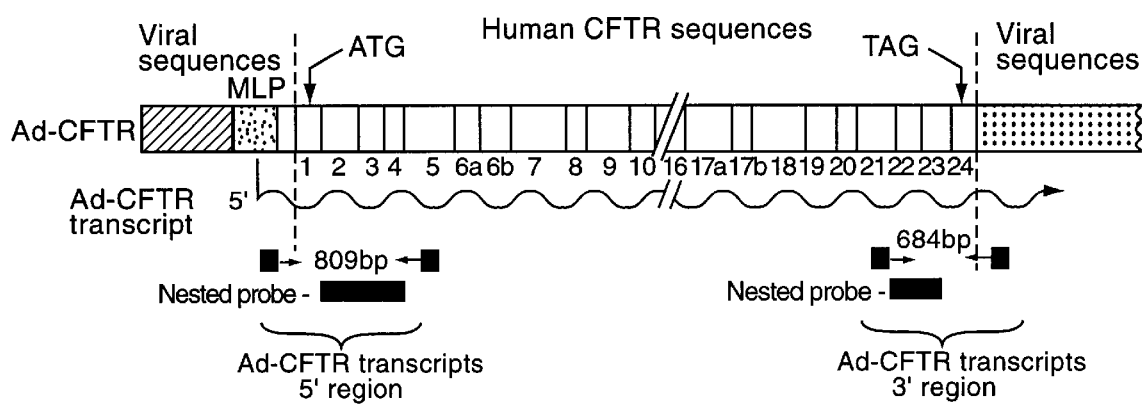
FIG. 4. Evaluation of the chronicity of human CFTR gene expression in cotton rat lung following in vivo infection with Ad-CFTR. Schematic of a portion of Ad-CFTR showing the Ad-CFTR-derived CFTR mRNA transcript and the location of primer pairs used to identify the Ad-CFTR-directed mRNA transcripts specifically. Ad-CFTR DNA sequences shown include (from the left): adenoviral expression cassette sequences (see FIG. 6 for details) including the major late promoter (MLP), the human CFTR cDNA coding sequence (CFTR exons are indicated by numbers below Ad-CFTR), and the remainder of the adenoviral vector genome. The Ad-CFTR transcript 5' amplification primer pair consists of a 5' viral-specific sense primer and a 3' human CFTR cDNA-specific antisense primer. The 3' primer pair consists of a 5' human CFTR cDNA-specific sense primer and a 3' viral-specific antisense primer. Also shown are the sizes of the expected amplification products and the "nested" probes used to detect specifically amplified Ad-CFTR transcripts. mRNA was converted to cDNA and amplified as described in Methods.
Figure 5A:
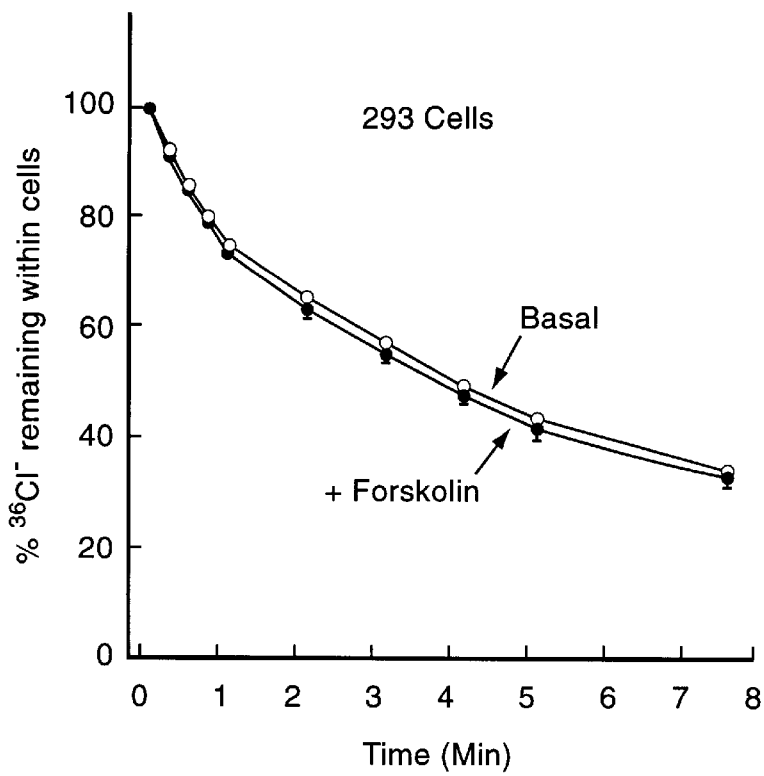
FIG. 5. In vitro Evaluation of the form and function of the human CFTR protein directed by Ad-CFTR. Panels A–G. Evaluation of the functional ability of Ad-CFTR-derived human CFTR to modulate forskolin-stimulated Cl$^-$ secretion. $^{36}$Cl$^-$ efflux was evaluated at rest (basal) and after stimulation (forskolin). The data are presented as % Cl$^-$ remaining in cells at each time point under basal or forskolin-stimulated conditions; each data point represents the mean of separate determinations (for each data point in panels A, B, and D, n=3; in panels C and E, n=4). Panels A and B. Evaluation of forskolin stimulated Cl$^-$ efflux in the 293 human embryonic kidney cells before and after infection with Ad-CFTR. A. Uninfected 293 cells. B. 293 cells infected with Ad-CFTR. Panels C and D. CFTR correction of the Cl$^-$ efflux defect in epithelial cells derived from an individual homozygous for the F508 CFTR mutation. Panel C. Uninfected CFPAC-1 cells. Panel D. CFPAC-1 cells infected with Ad-α1AT, as a negative control. Panel E. CFPAC-1 cells infected with Ad-CFTR.
Figure 5B:
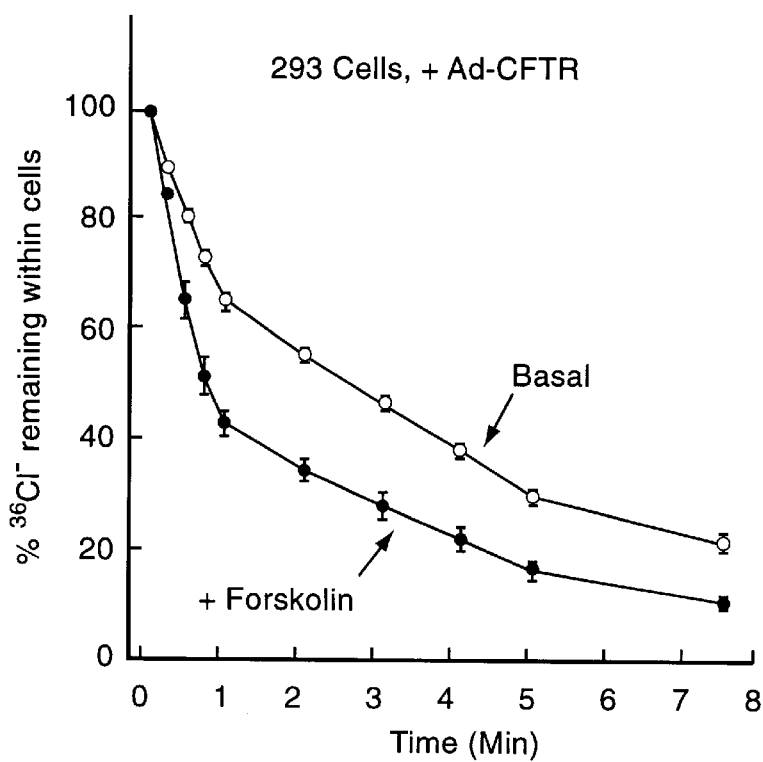
Figure 5C:
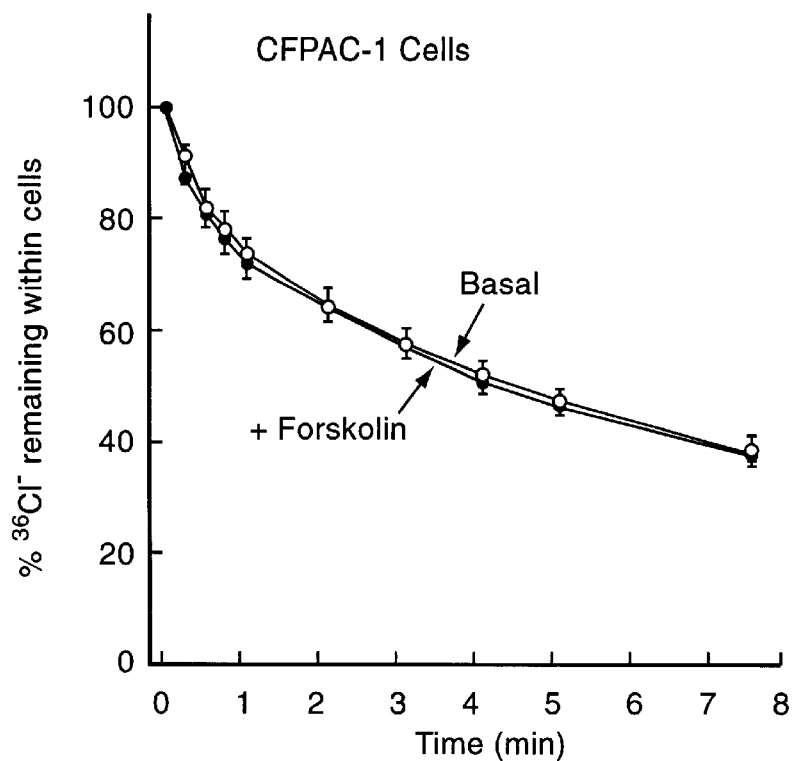
Figure 5D:
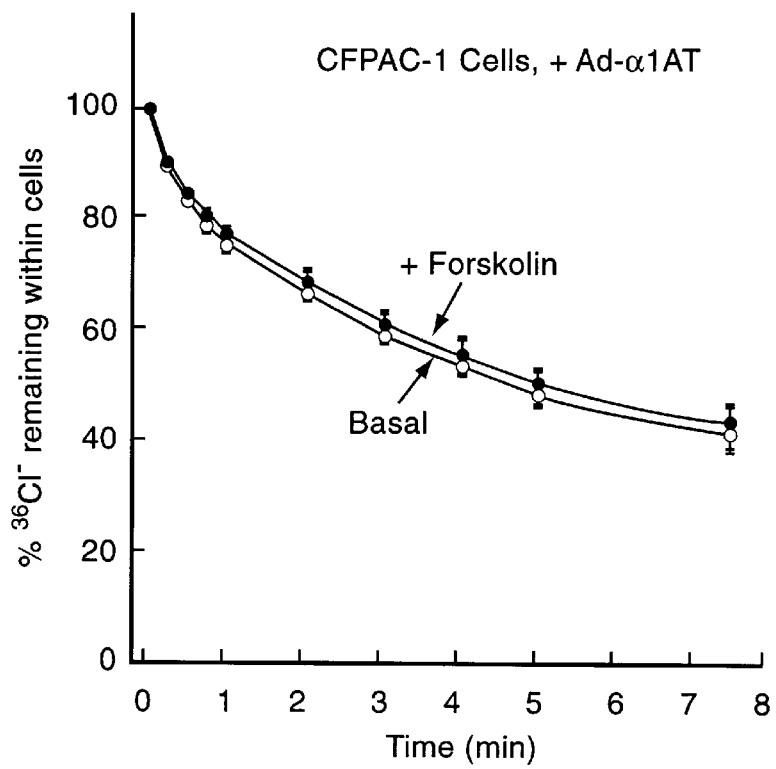
Figure 5E:
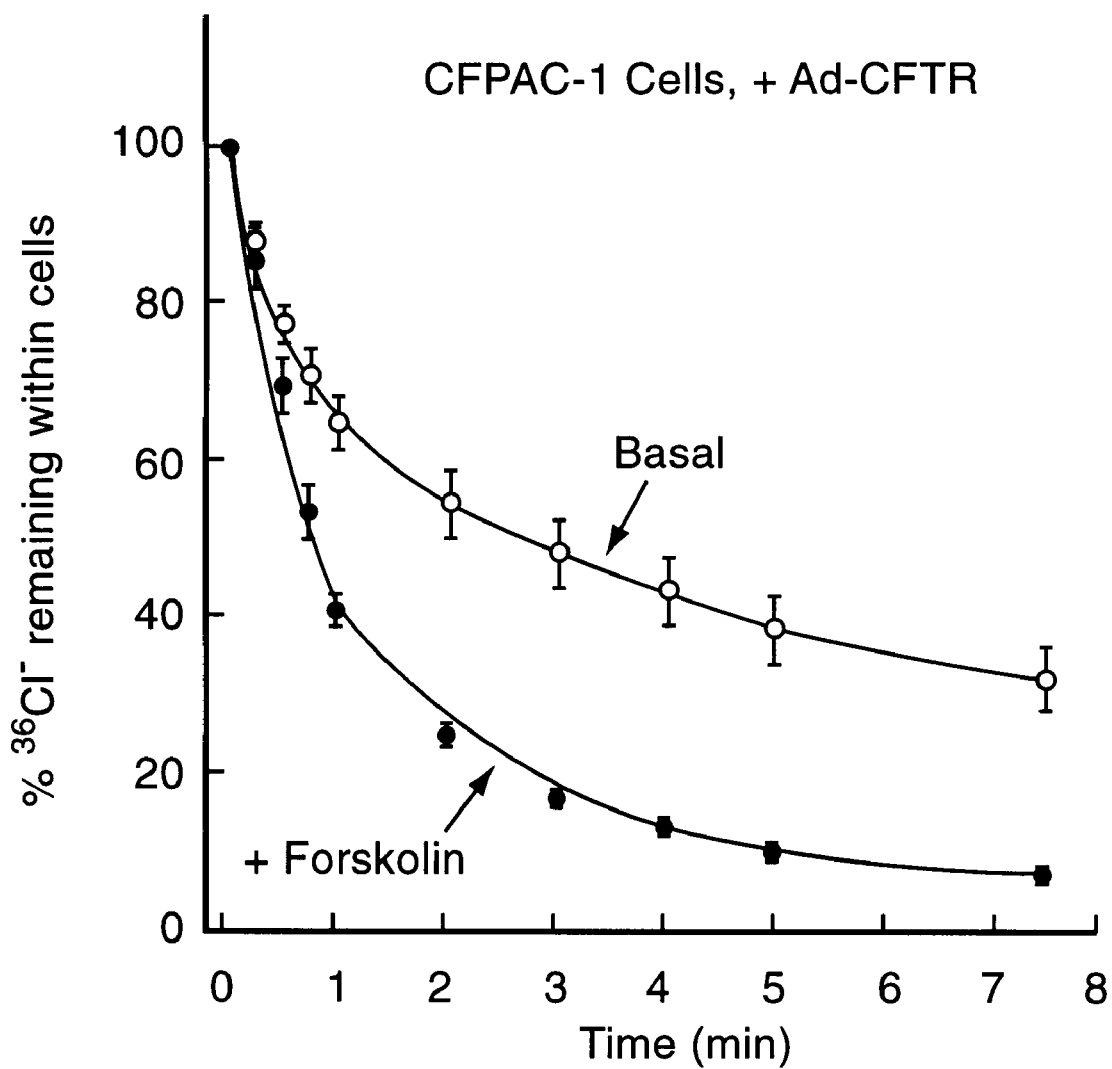

To further confirm the detection of human CFTR mRNA transcripts in the lungs of cotton rats infected with Ad-CFTR a strategy was employed which allows detection of only those transcripts with contiguous viral and human RNA sequences expected to be directed by Ad-CFTR. This was accomplished by amplification of Ad-CFTR mRNA (after conversion to cDNA) using the polymerase chain reaction (PCR) with two pairs of primers: (1) an adenoviral sense primer for viral sequences 5' to the viral/human CFTR junctional sequences and an opposing human CFTR cDNA antisense primer located within human CFTR exon 5; and (2) a human CFTR cDNA sense primer located within exon 21 and a viral antisense primer for SV40 viral sequences 3' to the human/viral RNA junctional sequences FIGS. 3, 4. To ensure that only RNA sequences were being detected and to exclude detection of potentially contaminating Ad-CFTR DNA, RNA samples were exposed to DNase I prior to conversion of purified RNA to cDNA and subsequent PCR. Further, each sample was evaluated in the absence or presence of reverse transcriptase. Ad-CFTR-directed human CFTR transcripts were detected using the 5' region primer-pair after Ad-CFTR infection, but not in uninfected animals or after Ad-dl312 infection. In the absence of reverse transcriptase, none of the samples amplified CFTR mRNA sequences. As a control, rat glyceraldehyde-3-phosphate dehydrogenase mRNA transcripts were detected in rat lung total RNA in all samples after incubation with reverse transcriptase, but not in the absence of reverse transcriptase.

The chronicity of Ad-CFTR-directed CFTR mRNA expression was demonstrated in cotton rat lung evaluated 2, 4, and 6 wk after in vivo infection with Ad-CFTR. Ad-CFTR-directed transcripts were observed at all time points with the 5' region amplification and also with the 3' region amplification. In the absence of reverse transcriptase, no samples showed amplification of CFTR sequences.

As there is no animal model for cystic fibrosis, it is not possible to evaluate the function of the Ad-CFTR-directed CFTR protein in vivo. However, the Ad-CFTR vector clearly directed the biosynthesis of functional CFTR protein as demonstrated by in vitro studies in cultured cells (FIG. 5). In this regard, the de novo biosynthesis of human CFTR protein was evaluated in cells modified in vitro by Ad-CFTR infection using metabolic labeling and immunoprecipitation of the CFTR protein with a mouse anti-human CFTR-specific monoclonal antibody. Evaluation of Ad- CFTR infected 293 cells demonstrated the presence of a new 165 kDa protein, and a minor 141 kDa protein neither of which were present in uninfected cells (lane 1). CFPAC-1 cells infected by Ad-CFTR also showed a new protein band of 165 kDa not present in Ad-α1AT infected or uninfected (not shown) cells. For both 293 and CFPAC-1 cells, the size of the major Ad-CFTR-directed protein (165 kDa) is within the range of the size detected in T84 cells (not shown) and that expected for a completely processed form of the glycosylated protein. (Riordan, J. R. et al. (1989) Science 245:1066–1073, Cheng, S. H. et al. (1990) Cell, 63:827–834, Kartner, N. et al. (1991) Cell 64:681–691.

The ability of Ad-CFTR to impart cAMP-regulated $Cl^-$ secretion to cells which do not normally exhibit cAMP-regulated $Cl^-$ secretion (293 cells) and to correct the defective cAMP-stimulated upregulation of $Cl^-$ secretion in epithelial cells derived from individuals with cystic fibrosis (CFPAC-1 cells), was evaluated by examining forskolin-stimulated $^{36}Cl^-$ efflux (FIGS. 5, panels A–E). Consistent with the lack of detectable endogenous CFTR mRNA expression, uninfected 293 cells lacked the ability to upregulate $Cl^-$ secretion in the presence of forskolin (panel A). In contrast, after Ad-CFTR infection, forskolin significantly stimulated $Cl^-$ secretion (panel C). As expected, uninfected CFPAC-1 cells or CFPAC-1 cells infected with the control virus Ad-α1AT (panel D) did not demonstrate forskolin-stimulated $Cl^-$ secretion. However, after in vitro infection with Ad-CFTR, CFPAC-1 cells had a significant increase in forskolin-stimulated $Cl^-$ secretion (panel E) indicating correction of the CF epithelial cell phenotype and thus the function of the Ad-CFTR-directed product.

All publications mentioned hereinabove are hereby incorporated in their entirety by reference. Additionally, Rosenfeld, M. A. et al (1991) Science 252:431–434 and Rosenfeld et al. "In vivo transfer and Expression of CFTR gene" in press are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A pharmaceutical composition comprising (a) a replication defective adenovirus comprising a deletion in the E1a, E1b, and E3 regions, and further comprising a DNA segment encoding the CFTR protein operatively linked to a promoter, and (b) a pharmaceutically acceptable carrier.

2. The pharmaceutical composition of claim 1, wherein said pharmaceutical composition, when administered to a lung of a mammal, causes the expression of a sufficient quantity of said protein to increase Cl⁻ secretion in said lung.

3. The pharmaceutical composition of claim 2, wherein said pharmaceutical composition is adapted for administration to said lung by local installation or through use of an aerosol.

4. A method of expressing a DNA segment encoding the CFTR protein in a lung of a mammal, comprising directly administering to the lung of the mammal a replication deficient adenoviral construct comprising a DNA segment encoding the CFTR protein operably linked to a promoter, wherein said adenoviral construct comprises a deletion in the E1a, E1b, and E3 regions of the adenoviral genome, under conditions such that said DNA segment is expressed and a sufficient quantity of said protein is thereby produced to increase Cl⁻ secretion in said lung.

5. The method of claim 4, wherein said lung is fibrotic.

6. The method of claim 4, wherein said mammal is a human.

7. The method of claim 4, wherein said administration is by direct instillation or through use of an aerosol.

8. A pharmaceutical composition comprising (a) a replication defective adenovirus comprising a deletion in the E1a E1b, and E3 regions, and further comprising a DNA segment encoding the α1AT protein operatively linked to a promoter, and (b) a pharmaceutically acceptable carrier.

9. The pharmaceutical composition of claim 8, wherein said pharmaceutical composition, when administered to a lung of a mammal, causes the expression of a sufficient quantity of said protein to make a detectable level of an antibody in said mammal.

10. The pharmaceutical composition of claim 9, wherein said pharmaceutical composition is adapted for administration to said lung by local installation or through use of an aerosol.

11. A method of expressing a DNA segment encoding the α1AT protein in a lung of a mammal, comprising directly administering to the lung of the mammal a replication deficient adenoviral construct comprising a DNA segment encoding the α1AT protein operably linked to a promoter, wherein said adenoviral construct comprises a deletion in the E1a, E1b, and E3 regions of the adenoviral genome, under conditions such that said DNA segment is expressed and a sufficient quantity of said protein is thereby produced to make a detectable level of an antibody in said mammal.

12. The method of claim 11, wherein said lung is deficient in α1AT.

13. The method of claim 11, wherein said mammal is a human.

14. The method of claim 11, wherein said administration is by direct instillation or through use of an aerosol.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:1:

AGCTGTTGGG GCTCGCGGTT GAGG      24

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear -continued

```
    (xi) SEQUENCE DESCRIPTION: SEQ ID NO:2:

CATCAAATTT GTTCAGGTTG TTGG                                                  24

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

AGTGGAGTGA TCAAGAAATA TGG                                                   23

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

GTAACCATTA TAAGCTGCAA TAAAC                                                 25

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

AATGCATCCT GCACCACCAA CTGC                                                  24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

GGAGGCCATG TAGGCCATGA GGTC                                                  24
```